United States Patent
Smith et al.

(10) Patent No.: US 11,692,174 B2
(45) Date of Patent: Jul. 4, 2023

(54) SYSTEMS, METHODS, AND APPARATUS FOR INDUCED PLURIPOTENT STEM CELL ISOLATION AND COMBINATORIAL PRODUCTION

(71) Applicant: Sapphiros AI Bio LLC, Boston, MA (US)

(72) Inventors: Robin Y. Smith, Boston, MA (US); Marcie A. Glicksman, Boston, MA (US)

(73) Assignee: Sapphiros AI Bio LLC, Boston, MA (US)

( * ) Notice: Subject to any disclaimer, the term of this patent is extended or adjusted under 35 U.S.C. 154(b) by 897 days.

(21) Appl. No.: 16/484,167

(22) PCT Filed: Feb. 8, 2018

(86) PCT No.: PCT/US2018/017424
§ 371 (c)(1),
(2) Date: Aug. 7, 2019

(87) PCT Pub. No.: WO2018/148409
PCT Pub. Date: Aug. 16, 2018

(65) Prior Publication Data
US 2019/0376047 A1    Dec. 12, 2019

Related U.S. Application Data

(60) Provisional application No. 62/456,374, filed on Feb. 8, 2017.

(51) Int. Cl.
| | | |
|---|---|---|
| *G01N 33/48* | (2006.01) | |
| *C12N 5/074* | (2010.01) | |
| *G16B 45/00* | (2019.01) | |
| *G16B 35/10* | (2019.01) | |
| *G01N 33/569* | (2006.01) | |

(52) U.S. Cl.
CPC ..... *C12N 5/0696* (2013.01); *G01N 33/56966* (2013.01); *G16B 35/10* (2019.02); *G16B 45/00* (2019.02); *C12N 2501/999* (2013.01); *C12N 2510/00* (2013.01); *C12N 2510/02* (2013.01)

(58) Field of Classification Search
None
See application file for complete search history.

(56) References Cited

U.S. PATENT DOCUMENTS

2010/0189690 A1* 7/2010 Buchholz ............... A61P 25/28
435/235.1
2014/0056860 A1    2/2014  Prieur et al.
2015/0309062 A1   10/2015  Covey et al.

OTHER PUBLICATIONS

Song, Zhihua, et al. "Efficient generation of hepatocyte-like cells from human induced pluripotent stem cells." Cell research 19.11 (2009): 1233-1242.*
International Preliminary Report on Patentability for International Application No. PCT/US2018/017424 dated Aug. 13, 2019.
International Search Report and Written Opinion for International Application No. PCT/US2018/017424 dated May 11, 2018.

* cited by examiner

*Primary Examiner* — Anna Skibinsky
(74) *Attorney, Agent, or Firm* — Foley Hoag LLP; Erik A. Huestis; Sameer K. Pai

(57) ABSTRACT

Described herein are various systems, methods, and apparatus for systematic creation of isolated homogeneous colonies of cells from vector-based lineages. The vector-based lineages may originate from multiple types of viral vector families (e.g., Paramyx-oviridae, Retroviridae, Parvoviridae) or non-natural engineered vectors or a plurality of vector combinations, for example. In certain embodiments, the isolated homogeneous colonies of cells are vector-free sub-colonies; in other embodiments, the isolated homogeneous colonies of cells are homogeneous vector sub-colonies. In other embodiments, vector mixed sub-colonies are created. The disclosed systems, methods, and apparatus are useful for inducible pluripotent stem cell (iPSC) production and work by selectively binding to one or more corresponding protein markers expressed on the surface of a cell that indicate that cellular reprogramming has occurred. Software is used to automate the purification and isolation of the iPSCs produced.

12 Claims, 10 Drawing Sheets

300

302 — RECEIVING, BY A PROCESSOR OF A COMPUTER DEVICE, DATA FROM THE DETECTION OF A PLURALITY OF CELL SURFACE MARKERS EXPRESSED ON THE SURFACE OF IPSCS

304 — DETERMINING, BY THE PROCESSOR, ONE OR MORE VECTORS CONTACTED TO THE COLONY OF CELLS BASED ON THE DETECTED CELL SURFACE MARKERS

306 — MAPPING BY THE PROCESSOR, THE DETERMINED ONE OR MORE VECTORS TO A LIST OF A PLURALITY OF CELL SURFACE MARKERS CONTAINED IN THE ONE OR MORE FILES OF THE STORAGE FACILITY

308 — MAPPING ONE OR MORE BINDING AGENTS CONTAINED IN AN ELECTRONIC COMPENDIUM HAVING A BINDING SPECIFICITY FOR EACH MAPPED CELL SURFACE MARKER

FIG. 3A

SYSTEMS, METHODS, AND APPARATUS FOR INDUCED PLURIPOTENT STEM CELL ISOLATION AND COMBINATORIAL PRODUCTION

CROSS REFERENCE TO RELATED APPLICATIONS

This application claims the benefit of U.S. Provisional Application No. 62/456,374 filed Feb. 8, 2017, the contents of which are hereby incorporated by reference herein in their entirety.

TECHNICAL FIELD

The invention relates generally to the isolation and production of induced pluripotent stem cells (iPSCs). More particularly, in certain embodiments, the invention relates to systems and methods to isolate and combinatorially produce iPSCs.

BACKGROUND

Over the past several years there has been a large increase in the volume and complexity of techniques used for the production of induced pluripotent stem cells (iPSCs). Currently, iPSCs are produced by inserting copies of stem cell-associated genes—e.g., Oct 3/4, Sox 2, Klf4, and c-Myc (or Oct 3/4, Sox 2, Nanog, and LIN28)—into specialized cells using viral vectors.

One of the results of utilizing a viral vector to create these specialized cells is the need to generate a vector-free line of cells for further use in studies. The time needed to derive vector-free iPSC's varies depending on the culture and passage conditions. These times can be considerable (e.g., up to 2 months) and require hand-picked colony selection and repeated single colony sub-cloning along with repetitive analytical techniques such as immunostaining or PCR protocols and gel electrophoresis. The major limitation for potential clinical applications is the integration of viral transgenes into the host genomes that can result in multiple insertions and risk of tumorigenicity (K. Okita, T. Ichisaka, and S. Yamanaka, "Generation of germline-competent induced pluripotent stem cells," Nature, vol. 448, no. 7151, pp. 313-317, 2007; K. Okita, Y. Matsumura, Y. Sato et al., "A more efficient method to generate integration-free human iPS cells," Nature Methods, vol. 8, no. 5, pp. 409-412, 2011).

A number of manual techniques exist to aid a researcher in achieving vector-free cell lines. For example, a researcher typically performs two months of bulk or pooled-clone passaging to achieve a vector free line. In a further example, a researcher performs single colony sub-cloning where she selects (102) a single colony to transfer to another plate (Passage #1). From that plate, the researcher selects (104) another single colony and transfers it to another plate (Passage #2). This is done repeatedly (102, 104, 106) to achieve a vector free line FIG. 1. This process is tedious and time consuming.

Thus, there remains a need for improved systems, methods, and apparatus for culturing and removal of viral vectors such as the type used for producing induced pluripotent stem cells, contained therein.

SUMMARY

Described herein are various systems, methods, and apparatus for systematic creation of isolated homogeneous colonies of cells from vector-based lineages. The vector-based lineages may originate from multiple types of viral vector families (e.g., Paramyxoviridae, Retroviridae, Parvoviridae) or non-natural engineered vectors or a plurality of vector combinations, for example. In certain embodiments, the isolated homogeneous colonies of cells are vector-free sub-colonies; in other embodiments, the isolated homogeneous colonies of cells are homogeneous vector sub-colonies. In other embodiments, vector mixed sub-colonies are created. The disclosed systems, methods, and apparatus are useful for inducible pluripotent stem cell (iPSC) production and work by selectively binding to one or more corresponding protein markers expressed on the surface of a cell that indicate that cellular reprogramming has occurred. Software is used to automate the purification and isolation of the iPSCs produced.

Advantageously, in addition to selectively binding to the vector-containing cells that are expressing one or more corresponding surface cell markers, embodiments of the present disclosure include systems and methods for simultaneously purifying and separating multiple heterogeneous mixtures of vector generated iPSC lines, across different vector families, and viral subtypes, including separation via multiple techniques such as single bead, column, serial, microfluidic channel, and magnetic bead separation techniques.

In addition to viral-based automated selection and separation of iPSC lines, custom non-natural engineered vectors can also be used for automatic selection and separation of iPSC lines. Embodiments of the present disclosure described herein also have utility in selection of iPSC types from a plurality of viral vectors (including non-natural engineered vectors) for use in diagnostic testing, cell therapy, analytical techniques, and cellular engineering.

Moreover, embodiments of the present disclosure provide tools that enable an individual to readily access vector-free colonies for further research investigations, diagnostics, or use in cell therapies or cellular engineering from a single or mixed culture of cells in an immediate timeframe compared with the current technique of multiple passaging and single colony sub cloning. These tools are beneficial to, for example, research managers at pharmaceutical companies, academic researchers, medical professionals practicing regenerative medicine, diagnostic clinics, and any molecular biologist utilizing induced pluripotent stem cells that require vector free colonies.

In one aspect, the invention is directed to a method for isolating and producing induced pluripotent stem cells (iPSCs), the method comprising: providing a colony of cells (e.g., somatic cells (e.g., hair cells, blood cells, fibroblasts)) having been contacted with one or more vectors (e.g., via multiple viral transfections) (e.g., wherein the one or more vectors comprises multiple vector (e.g., viral) families); detecting (e.g., via Fluorescence, 2D-electrophoresis or 2D-Chromatography, Mass Spectroscopy, Fluorescence-activated cell sorting (FACS)) a plurality of cell surface markers expressed on the surface of the iPSCs, wherein each of the plurality of cell surface markers is indicative of a vector (e.g., a viral vector, e.g., a non-natural engineered vector) contacted with the colony of cells; mapping, by a processor of a computer device, a plurality of candidate binding agents (e.g., wherein the plurality of candidate binding agents comprise an antibody, biotinylated bead, hydrophobic bead, magnetic nanoparticle, and combinations thereof) to the plurality of cell surface markers (e.g., wherein the plurality of corresponding candidate binding agents have binding specificity to the plurality of cell surface markers);

selecting at least one of the plurality of candidate binding agents for specific binding to at least one of the plurality of cell surface markers; contacting (e.g., mechanically) the colony of cells with one or more of the selected binding agents; and separating the iPSCs from the colony of cells (e.g., into vector-based lineages determined by mapped cell surface markers) (e.g., via single bead separation, column chromatography, serial separation, microfluidic channel separation, magnetic bead binding, antibody binding).

In certain embodiments, the method comprises determining, by the processor, a prescribed order in which the selected binding agents are to be contacted with the colony of cells for desired specific binding.

In certain embodiments, the method comprises displaying or causing to be displayed on a graphical user interface (GUI) module, by the processor, a representation of one or more separation methodologies (e.g., single bead separation, column chromatography, serial separation, microfluidic channel separation, magnetic bead binding, fluorescence activated cell (FACS) sorting and antibody binding) for separation of the iPSCs from the colony of cells using the selected binding agents.

In certain embodiments, the method comprises generating (e.g., culturing and colonizing) one or more isolated homogeneous colonies of iPSCs from a single vector lineage (e.g., wherein the one or more isolated homogeneous colonies of iPSCs are vector-free (e.g., via culturing)) (e.g., wherein the iPSCs comprise a genetic variant (e.g., gene insertion, gene deletion) compared to the colony of cells).

In certain embodiments, the GUI module displays, in a first designated location of the GUI display, a list of, and/or icon(s) representing one or more electronic files corresponding to the plurality of cell surface markers and/or candidate binding agents.

In certain embodiments, each of the one or more electronic files contains a plurality of vectors in a second designated location of the GUI display.

In certain embodiments, the GUI module displays, in a third designated location of the GUI display, a list of, and/or icon(s) representing the plurality of candidate binding agents mapped to the plurality of cell surface markers corresponding to the one or more electronic files listed and/or represented in the first designated location of the GUI display.

In another aspect, the invention is directed to a method for electronically determining and compiling a list of binding agents from a storage facility comprising one or more electronic files, the method comprising: receiving, by a processor of a computer device, data from the detection (e.g., via Fluorescence, 2D-electrophoresis or 2D-Chromatography, Mass Spectroscopy) of a plurality of cell surface markers expressed on the surface of iPSCs; determining, by the processor, one or more vectors (e.g., viral vectors, e.g., non-natural engineered vectors) contacted to the colony of cells based on the detected cell surface markers; mapping (e.g., electronically), by the processor, the determined one or more vectors to a list of a plurality of cell surface markers contained in the one or more files of the storage facility; and mapping one or more binding agents contained in an electronic compendium having a binding specificity for each mapped cell surface marker.

In certain embodiments, the method comprises displaying or causing to be displayed, by a processor of a computer device, in a first designated location of a graphical user interface module, a list of, and/or icon(s) representing one or more electronic files corresponding to the one or more binding agents mapped to the plurality of cell surface markers.

In another aspect, the invention is directed to a method comprising: providing a heterogeneous mixture of a plurality of colonies of cells (e.g., somatic cells (e.g., hair cells, blood cells, fibroblasts)) having been contacted with a plurality of vectors (e.g., viral vectors, e.g., non-natural engineered vectors) (e.g., via multiple viral transfections) (e.g., wherein the plurality of vectors comprises multiple vector (e.g., viral) families); producing a colony of iPSCs from the plurality of colonies of cells, wherein the colony of iPSCs comprises varied genetic edits (e.g., gene insertions, gene deletions); and separating the colony of iPSCs into one or more homogeneous vector lineages (e.g., based on cell surface marker) (e.g., via single bead separation, column chromatography, serial separation, microfluidic channel separation, magnetic bead binding, antibody binding).

In certain embodiments, the plurality of cell surface markers is produced by a type of vector family and/or vector (e.g., wherein the type of vector family comprises Paramyxoviridae virus vector family, Retroviridae virus vector family, Parvoviridae virus vector family, non-natural engineering vectors, and combinations thereof).

In certain embodiments, the plurality of cell surface markers is produced by Paramyxoviridae virus vector family and wherein the Paramyxoviridae virus vector family comprises one or more members selected from the group consisting of Atlantic salmon paramyxovirus, Newcastle disease virus, Mumps virus, Ferlavirus, Hendravirus, Nipahvirus, Measels, Sendai, Avian pneumovirus, Tioman virus, and TPMV-like virus.

In certain embodiments, the plurality of cell surface markers comprise one or more members selected from the group consisting of Nucleocapsid protein (NP), Phosphoprotein (P), Matrix protein (M), Fusion protein (F), and Hemagglutinin-Neuraminidase (HN), Large protein (L)).

In certain embodiments, the plurality of cell surface markers is produced by Retroviridae virus vector family and wherein the Retroviridae virus vector family comprises one or more members selected from the group consisting of Avian leukosis virus, Mouse mammary tumor virus, Murine leukemia virus, Feline leukemia virus, Bovine leukemia virus, Human T-lymphotropic virus, and lentivirus (e.g., the Human immunodeficiency virus 1).

In certain embodiments, the plurality of cell surface markers comprise one or more members selected from the group consisting of Capsid, Reverse Transcriptase, Integrase, Protease, p6, p7, p17, p24, gp41, and gp120.

In certain embodiments, the plurality of cell surface markers is produced by Parvoviridae virus vector family and wherein the Parvoviridae virus vector family comprises one or more members selected from the group consisting of Primate tetraparvovirus, Rodent protoparvovirus, Sesavirus, and Primate erythroparvovirus.

In certain embodiments, the plurality of cell surface markers comprise one or more members selected from the group consisting of virion proteins, VP1, VP2, VP3, VP4, VP5, Capsid, phospholipase A2, non-structural proteins (NS), NS1, and NS2.

In another aspect, the invention is directed to a method comprising: expanding a population of cells in a cell culture medium (e.g., iPSCs, e.g., primary cells, e.g., blood cells, e.g., peripheral blood mononuclear cells) greater than 15 days (e.g., at least 30 days, e.g., at least 60 days, e.g., at least 90 days); following the expanding step, isolating (e.g., enriching) the population of cells that express a cell surface marker of interest (e.g. CD71, e.g., CD35); and contacting (e.g., stockpiling a plurality of viral vector transfections across the population of cells) a plurality of viral vectors with the enriched population of cells (e.g., via a multi-well plate).

In certain embodiments, the method comprises following the contacting step, selecting (e.g., isolating) the enriched population of cells for a gene of interest (e.g., cell cycle genes).

Elements of embodiments involving one aspect of the invention (e.g., methods) can be applied in embodiments involving other aspects of the invention, and vice versa.

Definitions

In order for the present disclosure to be more readily understood, certain terms are first defined below. Additional definitions for the following terms and other terms are set forth throughout the specification.

In this application, the use of "or" means "and/or" unless stated otherwise. As used in this application, the term "comprise" and variations of the term, such as "comprising" and "comprises," are not intended to exclude other additives, components, integers or steps. As used in this application, the terms "about" and "approximately" are used as equivalents. Any numerals used in this application with or without about/approximately are meant to cover any normal fluctuations appreciated by one of ordinary skill in the relevant art. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

"Binding Agent": The term "binding agent", as used herein, refers to an entity or moiety that has specificity to a cell surface marker. In certain embodiments, binding agents comprise or are an antibody, biotinylated bead, hydrophobic bead, magnetic nanoparticle, and combinations thereof.

"Marker": The term "marker", as used herein, refers to an entity or moiety whose presence or level is a characteristic of a particular state or event. In some embodiments, presence or level of a particular marker may be characteristic of presence or stage of a disease, disorder, or condition. To give but one example, in some embodiments, the term refers to a gene expression product that is characteristic of a particular tumor, tumor subclass, stage of tumor, etc. Alternatively or additionally, in some embodiments, a presence or level of a particular marker correlates with activity (or activity level) of a particular signaling pathway, for example that may be characteristic of a particular class of tumors. The statistical significance of the presence or absence of a marker may vary depending upon the particular marker. In some embodiments, detection of a marker is highly specific in that it reflects a high probability that the tumor is of a particular subclass. Such specificity may come at the cost of sensitivity (i.e., a negative result may occur even if the tumor is a tumor that would be expected to express the marker). Conversely, markers with a high degree of sensitivity may be less specific that those with lower sensitivity. According to the present invention a useful marker need not distinguish tumors of a particular subclass with 100% accuracy.

"Peptide" or "Polypeptide" or "Protein": The term "peptide" or "polypeptide" or "protein", as used herein, refers to a string of at least two (e.g., at least three) amino acids linked together by peptide bonds. In certain embodiments, a polypeptide comprises naturally-occurring amino acids; alternatively or additionally, in certain embodiments, a polypeptide comprises one or more non-natural amino acids (i.e., compounds that do not occur in nature but that can be incorporated into a polypeptide chain; see, for example, http://www.cco.caltech.edu/~dadgrp/Unnatstruct.gif, which displays structures of non-natural amino acids that have been successfully incorporated into functional ion channels) and/or amino acid analogs as are known in the art may alternatively be employed). In certain embodiments, one or more of the amino acids in a protein may be modified, for example, by the addition of a chemical entity such as a carbohydrate group, a phosphate group, a farnesyl group, an isofarnesyl group, a fatty acid group, a linker for conjugation, functionalization, or other modification, etc. In certain embodiments, a cell surface marker comprises or is a "peptide" or "polypeptide".

"Sample": The term "sample", as used herein, refers to a biological sample obtained or derived from a source of interest, as described herein. In certain embodiments, a source of interest comprises an organism, such as a microbe, a plant, an animal, or a human. In certain embodiments, a biological sample is or comprises biological tissue or fluid. In certain embodiments, a biological sample may be or comprise bone marrow; blood; blood cells; ascites; tissue or fine needle biopsy samples; cell-containing body fluids; free floating nucleic acids (e.g., cell free DNA); sputum; saliva; urine; cerebrospinal fluid, peritoneal fluid; pleural fluid; lymph; gynecological fluids; skin swabs; vaginal swabs; oral swabs; nasal swabs; washings or lavages such as a ductal lavages or broncheoalveolar lavages; aspirates; scrapings; bone marrow specimens; tissue biopsy specimens; surgical specimens; feces, other body fluids, secretions, and/or excretions; and/or cells therefrom, etc. In certain embodiments, a biological sample is or comprises cells obtained from an individual. In certain embodiments, obtained cells are or include cells from an individual from whom the sample is obtained. In certain embodiments, a sample is a "primary sample" obtained directly from a source of interest by any appropriate means. For example, in certain embodiments, a primary biological sample is obtained by methods selected from the group consisting of a swab, biopsy (e.g., fine needle aspiration or tissue biopsy), surgery, collection of body fluid (e.g., blood, lymph, feces etc.), etc. In certain embodiments, as will be clear from context, the term "sample" refers to a preparation that is obtained by processing (e.g., by removing one or more components of and/or by adding one or more agents to) a primary sample. For example, filtering using a semi-permeable membrane. Such a processed "sample" may comprise, for example nucleic acids or proteins extracted from a sample or obtained by subjecting a primary sample to techniques such as amplification or reverse transcription of mRNA, isolation and/or purification of certain components, etc.

"Specific": The term "specific, as used herein, refers an agent having an activity, is understood to mean that the agent discriminates between potential target entities or states. For example, in some embodiments, an agent is said to bind "specifically" to its target if it binds preferentially with that target in the presence of one or more competing alternative targets. In many embodiments, specific interaction is dependent upon the presence of a particular structural feature of the target entity (e.g., a nucleotide sequence, an epitope, a cleft, a binding site). It is to be understood that specificity need not be absolute. In certain embodiments, specificity may be evaluated relative to that of the binding agent for one or more other potential target entities (e.g., competitors). In certain embodiments, specificity is evaluated relative to that of a reference specific binding agent. In certain embodiments specificity is evaluated relative to that of a reference non-specific binding agent. In certain embodiments, the agent does not detectably bind to the competing alternative target(s) under conditions of binding to its target entity. In certain embodiments, the agent binds with higher on-rate, lower off-rate, increased affinity, decreased dissociation, and/or increased stability to its target entity as compared with the competing alternative target(s).

"Somatic cells": As used herein, the phrase "somatic cells" refers to any cells of the body (e.g., blood cell, hair cell, fibroblast cell) except germline cells (e.g., sperm, e.g., egg).

"Substantially": As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

"Therapeutic agent": As used herein, the phrase "therapeutic agent" refers to any agent that has a therapeutic effect and/or elicits a desired biological and/or pharmacological effect, when administered to a subject.

"Treatment": As used herein, the term "treatment" (also "treat" or "treating") refers to any administration of a substance that partially or completely alleviates, ameliorates, relieves, inhibits, delays onset of, reduces severity of, and/or reduces incidence of one or more symptoms, features, and/or causes of a particular disease, disorder, and/or condition. Such treatment may be of a subject who does not exhibit signs of the relevant disease, disorder, and/or condition and/or of a subject who exhibits only early signs of the disease, disorder, and/or condition. Alternatively or additionally, such treatment may be of a subject who exhibits one or more established signs of the relevant disease, disorder, and/or condition. In certain embodiments, treatment may be of a subject who has been diagnosed as suffering from the relevant disease, disorder, and/or condition. In certain embodiments, treatment may be of a subject known to have one or more susceptibility factors that are statistically correlated with increased risk of development of the relevant disease, disorder, and/or condition. In certain embodiments, treatment comprises delivery of therapeutics, including but not limited to, small molecule delivery, radiotherapy, immunotherapy, intrinsic therapeutic properties (e.g., ferroptosis), and particle-driven regulation of the tumor microenvironment. In certain embodiments, therapeutics are attached to particles, such as those described herein.

"Vector": As used herein, the term "vector" refers to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "expression vectors."

Drawings are presented herein for illustration purposes, not for limitation.

BRIEF DESCRIPTION OF DRAWINGS

The foregoing and other objects, aspects, features, and advantages of the present disclosure will become more apparent and better understood by referring to the following description taken in conduction with the accompanying drawings, in which:

FIG. 3A shows a method for electronically determining and compiling a list of binding agents from a storage facility comprising one or more electronic files, according to an illustrative embodiment of the invention.

DETAILED DESCRIPTION

Figure 1:
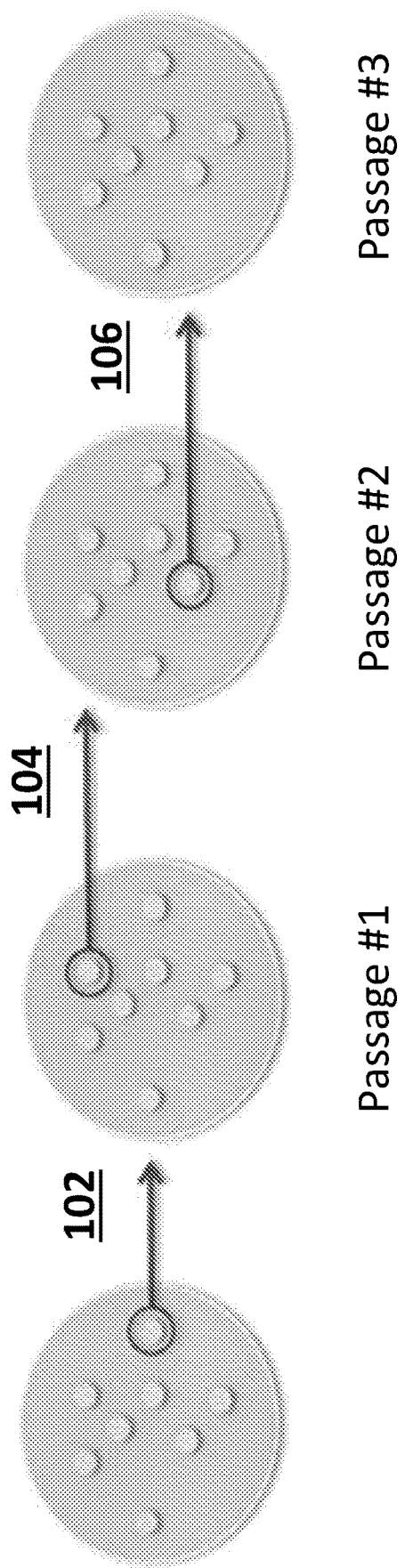
FIG. 1 shows a diagram and example of how single colony selection is performed.

Throughout the description, where compositions are described as having, including, or comprising specific components, or where methods are described as having, including, or comprising specific steps, it is contemplated that, additionally, there are compositions of the present invention that consist essentially of, or consist of, the recited components, and that there are methods according to the present invention that consist essentially of, or consist of, the recited processing steps.

It should be understood that the order of steps or order for performing certain action is immaterial so long as the invention remains operable. Moreover, two or more steps or actions may be conducted simultaneously.

The mention herein of any publication, for example, in the Background section, is not an admission that the publication serves as prior art with respect to any of the claims presented herein. The Background section is presented for purposes of clarity and is not meant as a description of prior art with respect to any claim. Headers are provided for the convenience of the reader and are not intended to be limiting with respect to the claimed subject matter.

Described herein are various systems, methods, and apparatus for systematic creation of isolated homogeneous colonies of cells from vector-based lineages. The vector-based lineages may originate from multiple types of viral vector families (e.g., Paramyxoviridae, Retroviridae, Parvoviridae) or non-natural engineered vectors or a plurality of vector combinations, for example. In certain embodiments, the isolated homogeneous colonies of cells are vector-free sub-colonies; in other embodiments, the isolated homogeneous colonies of cells are homogeneous vector sub-colonies. In other embodiments, vector mixed sub-colonies are created. The disclosed systems, methods, and apparatus are useful for inducible pluripotent stem cell (iPSC) production and work by selectively binding to one or more corresponding protein markers expressed on the surface of a cell that indicate that cellular reprogramming has occurred. Software is used to automate the purification and isolation of the iPSCs produced.

Advantageously, in addition to selectively binding to the vector-containing cells that are expressing one or more corresponding surface cell markers, embodiments of the present disclosure include systems and methods for simultaneously purifying and separating multiple heterogeneous mixtures of vector generated iPSC lines, across different vector families, and viral subtypes, including separation via multiple techniques such as single bead, column, serial, microfluidic channel, and magnetic bead separation techniques.

In addition to viral-based automated selection and separation of iPSC lines, custom non-natural engineered vectors can also be used for automatic selection and separation of iPSC lines. In certain embodiments, non-natural engineered vectors comprise engineered viral vectors as described herein. For example, a non-natural vector comprises a viral vector that has been engineered to express a cell surface marker (e.g., cell surface protein) that the vector does not naturally express and/or is not naturally expressed by the cell to be reprogrammed. Embodiments of the present disclosure described herein also have utility in selection of iPSC types from a plurality of viral vectors (including non-natural engineered vectors) for use in diagnostic testing, cell therapy, analytical techniques and cellular engineering.

Moreover, embodiments of the present disclosure provide tools that enable an individual to readily access vector-free colonies for further research investigations, diagnostics, or use in cell therapies or cellular engineering from a single or mixed culture of cells in an immediate timeframe compared with the current technique of multiple passaging and single colony sub cloning. These tools are beneficial to, for example, research managers at pharmaceutical companies, academic researchers, medical professionals practicing regenerative medicine, diagnostic clinics, and any molecular biologist utilizing induced pluripotent stem cells that require vector free colonies.

In general, embodiments of the present disclosure identify and compile viral vectors for creation of iPSCs. In certain embodiments, a listing of cell surface markers that can be expressed onto iPSCs caused by contacting a vector or a plurality of vectors to a colony of cells (e.g., somatic cells (e.g., derived from a sample)) is utilized to determine which set of those cell surface markers are present on the surface of the reprogrammed iPSCs. In certain embodiments, the set of surface markers is used to identify a corresponding binding agent that can be used for selective binding to and isolation of the reprogrammed iPSCs.

Embodiments of the present disclosure include a set of identified candidate materials ("binding agents") to selectively bind to the associated set of surface cell markers (e.g., for each identified candidate protein there is a corresponding candidate binding agent such as an antibody, biotinylated beads, hydrophobic beads, and magnetic cell isolation). Once the candidate materials are identified as having the proper selectivity to the identified proteins, the candidate cells (e.g., those cells having been infected (e.g., contacted) with viral or non-natural vectors for cellular reprogramming) are then separated via one or more techniques including, for example, single bead separation, column chromatography, serial separation, microfluidic channel separation, magnetic bead binding, and antibody binding. In certain embodiments, the candidate cells are separated via a plurality of techniques.

In certain embodiments, a plurality of binding agents is employed and the combinatorial separation and isolation takes place as the cells expressing the corresponding surface cell markers are isolated. The process can be repeated with a multiplicity of corresponding binding agents to create isolated homogeneous colonies of one vector lineage resulting in vector-free, vector-mixed, and homogeneous vector sub-colonies.

In certain embodiments, the iPSCs produced and isolated may be employed as a therapeutic agent or treatment for one or more diseases, disorders, and/or conditions.

Exemplary Apparatus for Isolation and Combinatorial Production of iPSCs

In certain embodiments, the original vector lineage is recognized and identified from manual entry into a computational system. In certain embodiments, an apparatus is used to perform surface protein analysis (e.g., via Fluorescence, 2D-electrophoresis or 2D-Chromatography, Mass Spec, Fluorescence-activated cell sorting (FACS)) in order to automatically identify the type of viral vector utilized for cellular reprogramming (e.g., via corresponding to cell surface marker(s) present on the surface of the reprogrammed cells). In certain embodiments, the apparatus identifies one or more binding agents corresponding to the cell surface markers for specific binding and isolation of the reprogrammed iPSCs. In certain embodiments, the apparatus comprises a liquid handler that is capable of liquid aspiration and handling.

In certain embodiments, the apparatus includes a memory for storing code defining the set of instructions for determining parameters for a plurality of binding agents and sequence of addition of said binding agents, and a processor for executing the set of instructions as well as liquid handling apparatus for application of binding agents to the colonies analyzed. The code includes a graphical user interface (GUI) module that displays, in a first designated location of a GUI display, one or more of the identified vectors from an electronic search of a storage facility that stores one or more electronic files corresponding to those vectors. Each of the displayed items matches to a system identified vector and/or cell surface markers corresponding to those vectors. The graphical user interface module also displays, in a second designated location of the GUI display, a list of, and/or icon(s) representing, one or more electronic files corresponding to the identified cell surface markers and/or binding agents from the storage facility. Each such file contains one or more of the vectors in the first designated location of the GUI display. Moreover, the graphical user interface module displays, in a third designated location of the GUI display, a list of, and/or icon(s) representing, binding agents of a selected protein corresponding to the electronic files listed and/or represented in the second designated location of the GUI display.

In general, embodiments of the present disclosure provide for electronically identifying and compiling a list of potential binding agents found in a storage facility comprising one or more electronic files. For example, the present disclosure provides for identifying the vector type used via various analytical techniques, and electronically matching those vectors to corresponding cell marker proteins that are expressed in those cell colonies via a plurality of candidate proteins in the electronic files of the storage facility. For each identified cell surface marker, the disclosure provides for searching an electronic compendium of identified binding agents to that cell surface marker, displaying the methodology for colony separation on a graphical user interface, and a methodology for mechanically introducing a plurality of binding substances to the colony for selective binding and isolation.

Figure 2:
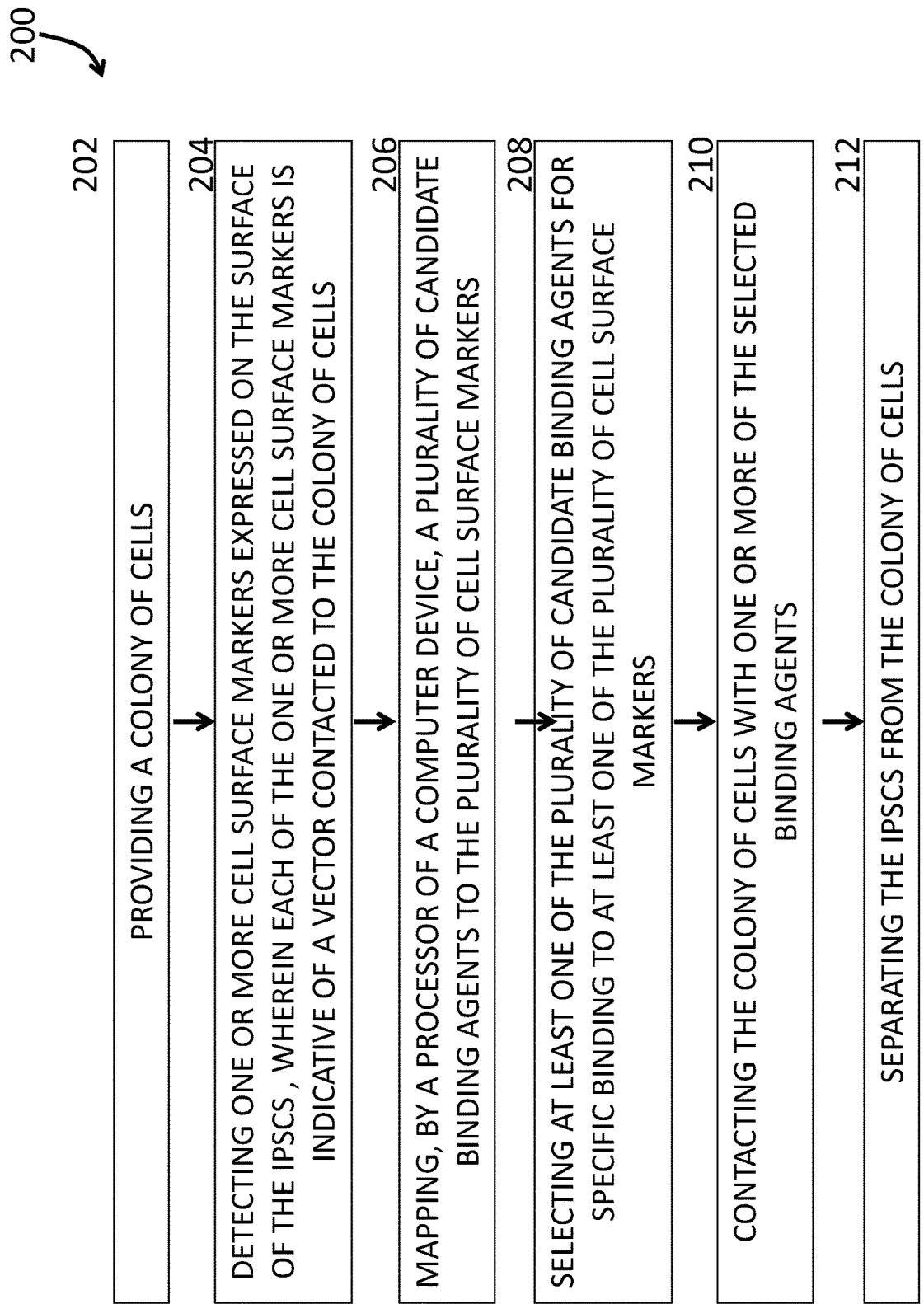
FIG. 2 shows a method for isolating and producing induced pluripotent stem cells (iPSCs), according to an illustrative embodiment of the invention.

FIG. 2 shows an example process 200 for isolating and producing induced pluripotent stem cells (iPSCs). In one step 202, a colony of cells is provided, the colony having been contacted with one or more vectors. Contacting the colony of cells with the one or more vectors may produce iPSCs within the colony. In order to separate out the produced iPSCs, in another step 204, one or more cell surface markers expressed on the surface of the iPSCs are detected as described herein. The detected cell surface markers are indicative of the vectors with which the colony of cells was contacted to produce iPSCs. In another step 206, a plurality of candidate binding agents are mapped to the detected cell surface markers, for example via a computer process. Binding agents that bind specifically to the detected cell surface markers are selected (208) and contacted to the colony of cells (210). The specific binding between the selected binding agents and the cell surface markers expressed by the various iPSCs may be used to separate the iPSCs from the colony of cells (212).

Turning to FIG. 3A, in certain embodiments a list of binding agents from a storage facility is determined and compiled (e.g., automatically). In the example process 300 of FIG. 3A, in one step 302, data from detection of a plurality of cell surface markers expressed on the surface of the iPSCs is received. In another step 304, the one or more vectors contacted to the colony of cells based on the detected cell surface markers are determined. In another step 306, the determined one or more vectors are mapped to a list of a plurality of cell surface markers contained in the one or more files of the storage facility. In another step 308, for each mapped cell surface marker, one or more binding agents contained in an electronic compendium are identified (e.g., mapped to the cell surface marker(s)).

Figure 3B:
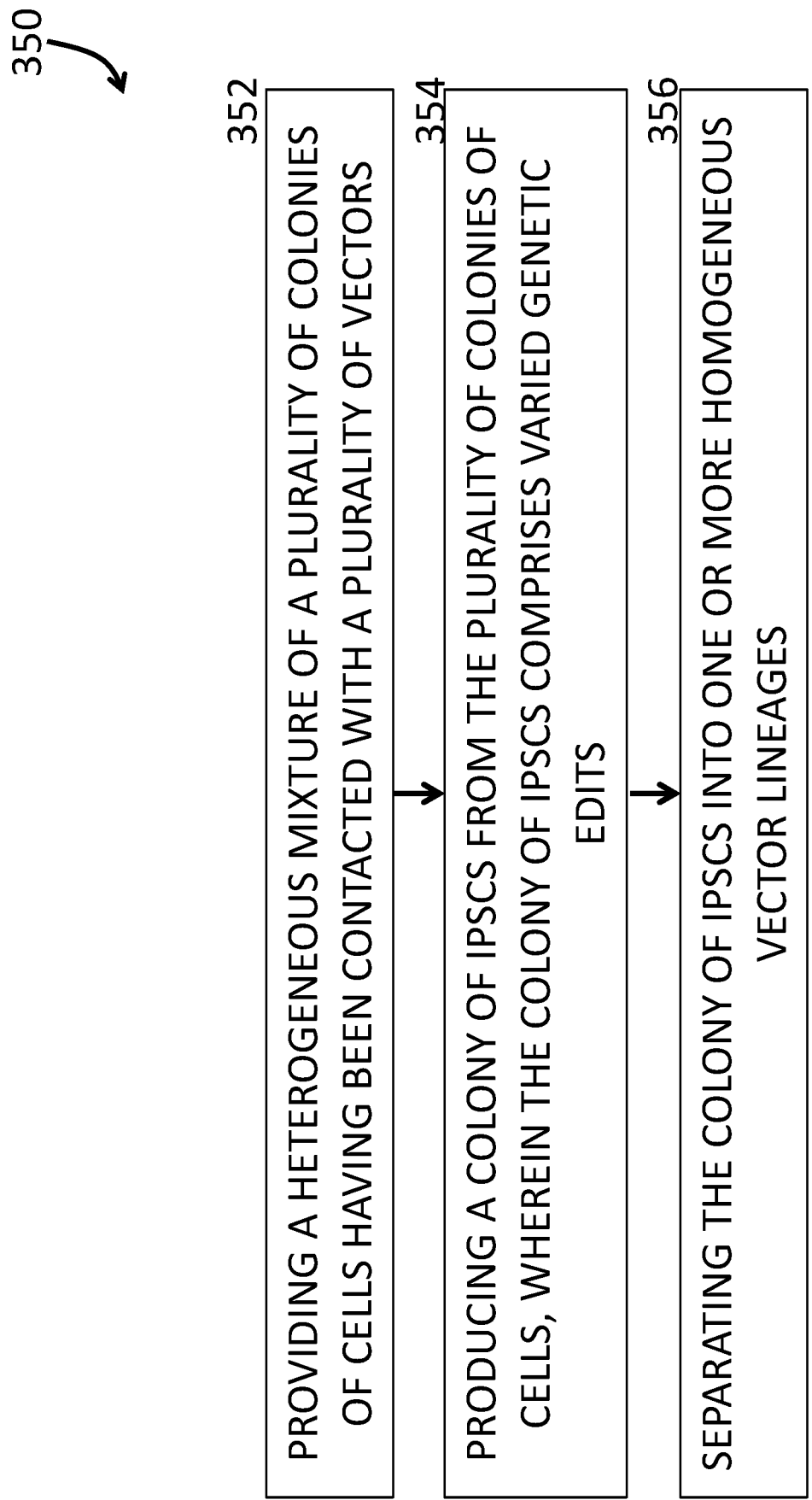
FIG. 3B shows a method of separating a colony of iPSCs into one or more homogeneous vector lineages, according to an illustrative embodiment of the invention.

In certain embodiments, iPSCs may be separated into one or more homogeneous vector lineages. FIG. 3B shows an example process 350 for separating iPSCs into one or more homogeneous vector lineages. In one step 352, a heterogeneous mixture of a plurality of colonies of cells (e.g., having been contacted with a plurality of vectors) is provided. A colony of iPSCs comprising varied genetic edits may be produced from the heterogeneous mixture of plurality of colonies of cells (354). In another step 356, the colony of iPSCs may be separated into one or more homogeneous vector lineages (356).

Exemplary Viral Vectors

In certain embodiments, a vector family includes Paramyxoviridae, Retroviridae, or Parvoviridae.

Subfamilies of Paramyxoviridae include several viral species (e.g., Atlantic salmon paramyxovirus, Newcastle disease virus, Mumps virus, Ferlavirus, Hendravirus, Nipahvirus, Measels, Sendai, Avian pneumovirus, Tioman virus, and TPMV-like viruses). For example, the use of Sendai virus from the family Paramyxoviridae is one common type of vector utilized in the production of iPSCs that results in a non-integrative (e.g., does not integrate and/or recombine with genetic DNA of the cell) induced pluripotent stem cell line.

Subfamilies of Retroviridae include several viral species (e.g., Avian leukosis virus, Mouse mammary tumor virus, Murine leukemia virus, Feline leukemia virus, Bovine leukemia virus, Human T-lymphotropic virus, and Lentivirus such as the Human immunodeficiency virus 1). For example, vectors based on the human immunodeficiency virus (HIV) provide an effective means for the delivery, integration, and expression of exogenous genes in mammalian cells and are used in production of iPSCs.

Subfamilies of Parvoviridae include several viral species (e.g., Primate tetraparvovirus, Rodent protoparvovirus, Sesavirus, Primate erythroparvovirus 1).

Exemplary Cell Surface Markers

In certain embodiments, the viral vector is identified by corresponding cell surface markers. For example, iPSCs reprogrammed via Sendai virus feature corresponding cell surface markers enumerated for the particular family of Paramyxoviridae.

In certain embodiments, cell surface markers for family Paramyxoviridae include Nucleocapsid protein (NP), Phosphoprotein (P), Matrix protein (M), Fusion protein (F), Hemagglutinin-Neuraminidase (HN), and Large protein (L). In certain embodiments, the identified cell surface markers are matched to corresponding binding agents. In certain embodiments, cell surface markers of Retroviridae include Capsid and Env proteins.

In certain embodiments, cell surface markers of Parvoviridae viruses include virion proteins, VP1, VP2, VP3, VP4, VP5, Capsid, phospholipase A2, non-structural proteins (NS), NS1, or NS2.

Isolation and Combinatorial Production of iPSCs via a Plurality of Viral Vectors In certain embodiments, an iPSC colony is created from a plurality of viral vectors that express a corresponding plurality of cell surface markers. For example, in a mixture of iPSCs produced by a mixture of Sendai and Lentiviral vectors in combination, the Sendai cell surface markers of Paramyxoviridae (e.g., Nucleocapsid protein (NP), Phosphoprotein (P), Matrix protein (M), Fusion protein (F), Hemagglutinin-Neuraminidase (HN), and Large protein (L)) are identified as well as the Lentiviral cell surface markers of Retroviridae (e.g., Capsid, Reverse Transcriptase, Integrase, Protease, p6, p7, p17, p24, gp41, and gp120). In certain embodiments, the iPSCs are produced by any two or more different viral vector family combinations.

In certain embodiments, a heterogeneous mixture of cell colonies is created from a plurality of viral vectors to combinatorially create engineered cell colonies of varied genetic edits or insertions while retaining the ability to separate the resulting homogeneous lineages after cell culture and colonization.

Figure 6:
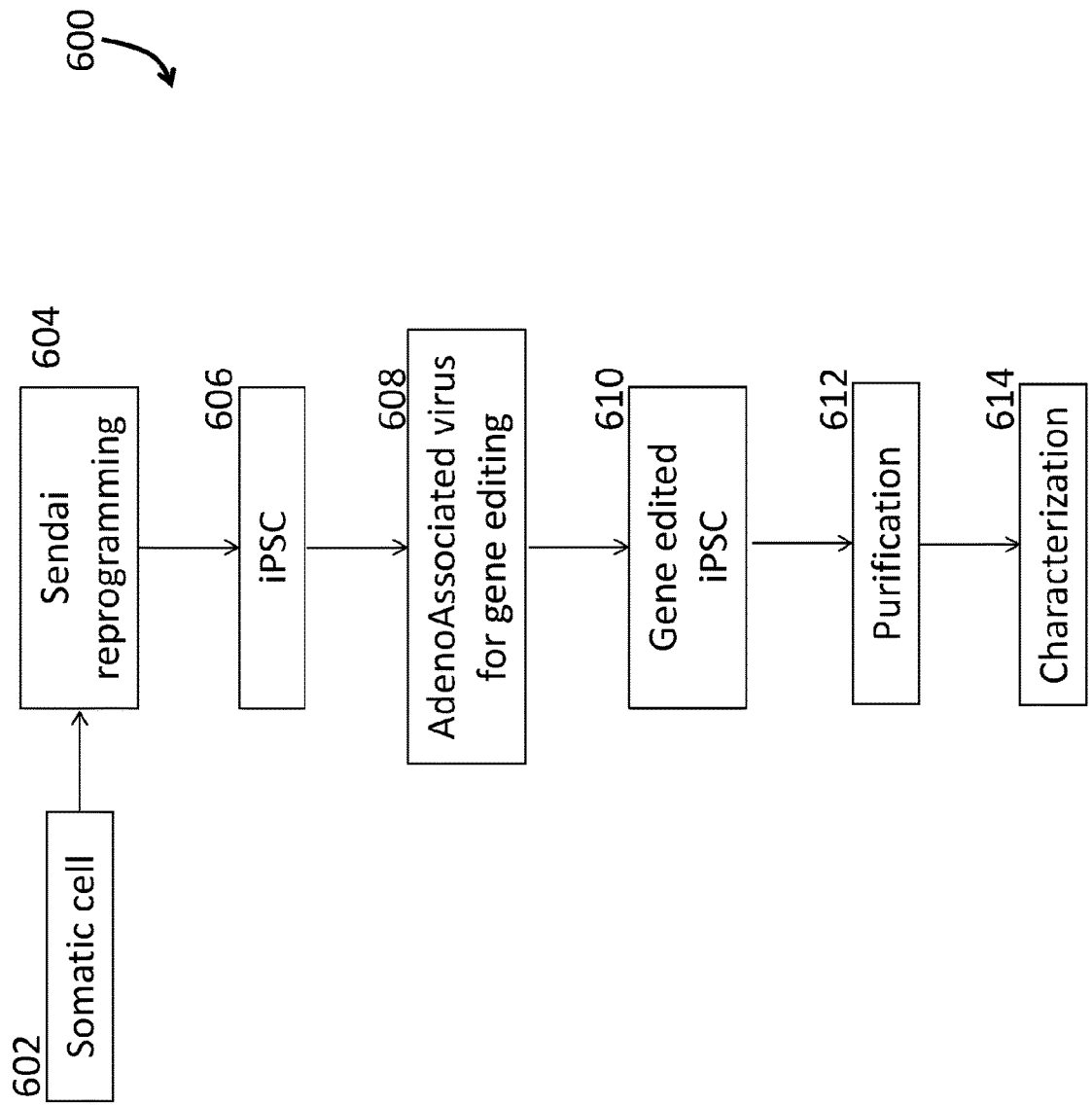
FIG. 6 shows diagram for purification and characterization of multiple viral transfections, according to an illustrative embodiment of the invention.

For example, in certain embodiments, the present disclosure provides for purification of multiple viral transfections. An example process 600 is shown in FIG. 6. For example, a somatic cell 602 can be reprogrammed to iPSC using Sendai virus 604. The resulting iPSCs 606 are genetically engineered (e.g., to insert a gene (e.g., to have a gain of function), to correct a gene, or remove a gene (e.g., to have a loss of function)) using AdenoAssociated Virus 608. In certain embodiments, the iPSCs are genetically engineered via a nuclease (e.g., a wild-type nuclease, e.g., an engineered nuclease) (e.g., a zinc-finger nucleases (ZFNs), a transcription activator-like effector nucleases (TALEN), a CRISPR/Cas9) 610.

The heterogeneous population can be purified 612 and characterized (e.g., genotyped) 614 for desired cellular properties as shown in FIG. 6.

In certain embodiments, a plurality of viral vector transfections are stockpiled across a population of cells. FIG. 9 shows an example process 900 for this stockpiling approach. In particular, in certain embodiments, a population of cells is expanded in a cell culture medium for at least 15 days (902). Following this expansion step, the population of cells that express a particular cell surface marker of interest is isolated (904). The isolated population of cells may be contacted with a plurality of viral vectors (e.g., to generate iPSCs)(906). A constructive example of an embodiment of this approach is described herein with respect to FIG. 7 and FIG. 8.

Illustrative Network Environment

Figure 4:
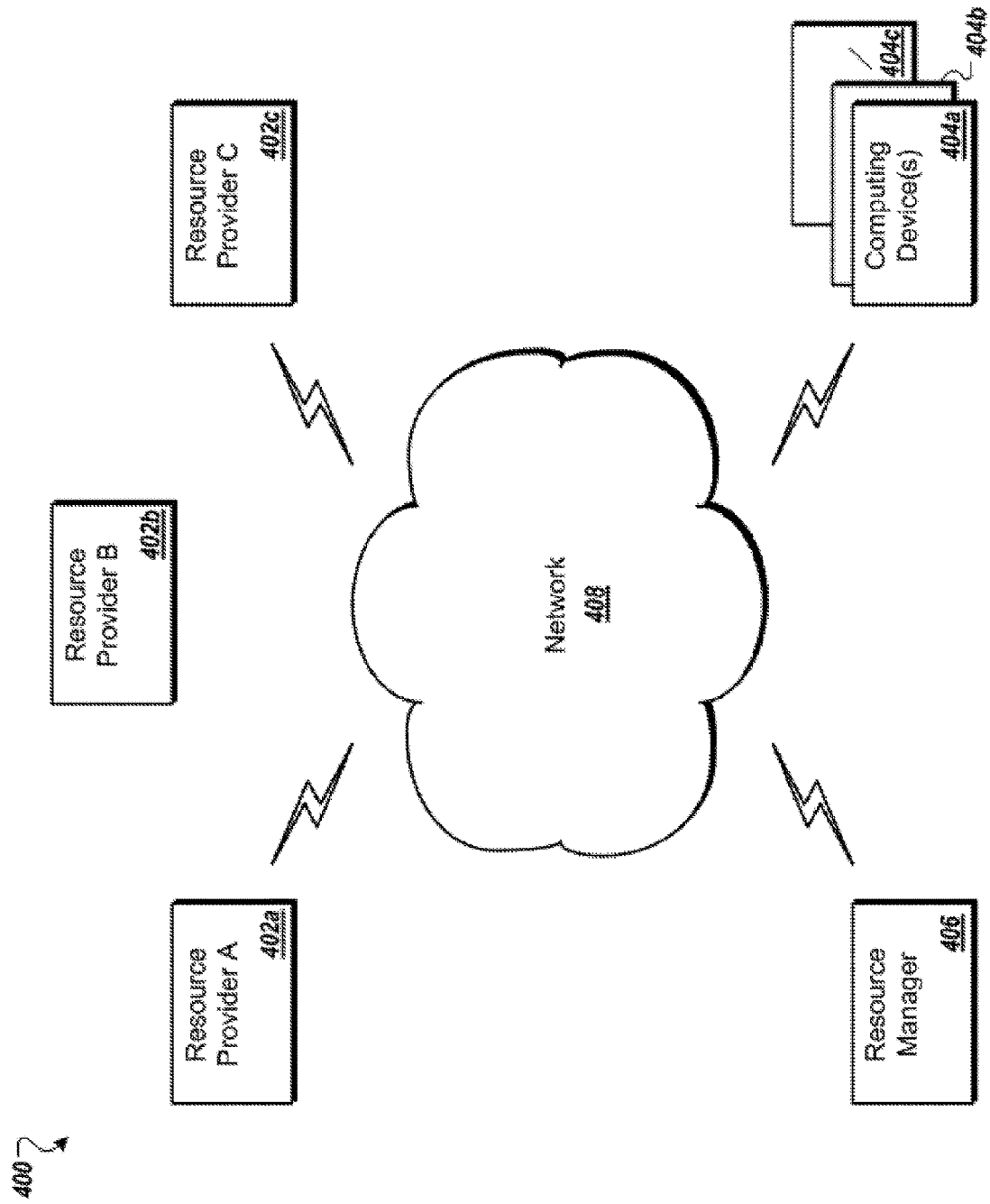
FIG. 4 is a block diagram of an example network environment for use in the methods and systems for induced pluripotent stem cell isolation and combinatorial production, according to an illustrative embodiment.

FIG. 4 shows an illustrative network environment 400 for use in the methods and systems for induced pluripotent stem cell isolation and combinatorial production, as described herein. In brief overview, referring now to FIG. 4, a block diagram of an exemplary cloud computing environment 400 is shown and described. The cloud computing environment 400 may include one or more resource providers 402a, 402b, 402c (collectively, 402). Each resource provider 402 may include computing resources. In some implementations, computing resources may include any hardware and/or software used to process data. For example, computing resources may include hardware and/or software capable of executing algorithms, computer programs, and/or computer applications. In some implementations, exemplary computing resources may include application servers and/or databases with storage and retrieval capabilities. Each resource provider 402 may be connected to any other resource provider 402 in the cloud computing environment 400. In some implementations, the resource providers 402 may be connected over a computer network 408. Each resource provider 402 may be connected to one or more computing device 404a, 404b, 404c (collectively, 404), over the computer network 408.

The cloud computing environment 400 may include a resource manager 406. The resource manager 406 may be connected to the resource providers 402 and the computing devices 404 over the computer network 408. In some implementations, the resource manager 406 may facilitate the provision of computing resources by one or more resource providers 402 to one or more computing devices 404. The resource manager 406 may receive a request for a computing resource from a particular computing device 404. The resource manager 406 may identify one or more resource providers 402 capable of providing the computing resource requested by the computing device 404. The resource manager 406 may select a resource provider 402 to provide the computing resource. The resource manager 406 may facilitate a connection between the resource provider 402 and a particular computing device 404. In some implementations, the resource manager 406 may establish a connection between a particular resource provider 402 and a particular computing device 404. In some implementations, the resource manager 406 may redirect a particular computing device 404 to a particular resource provider 402 with the requested computing resource.

Figure 5:
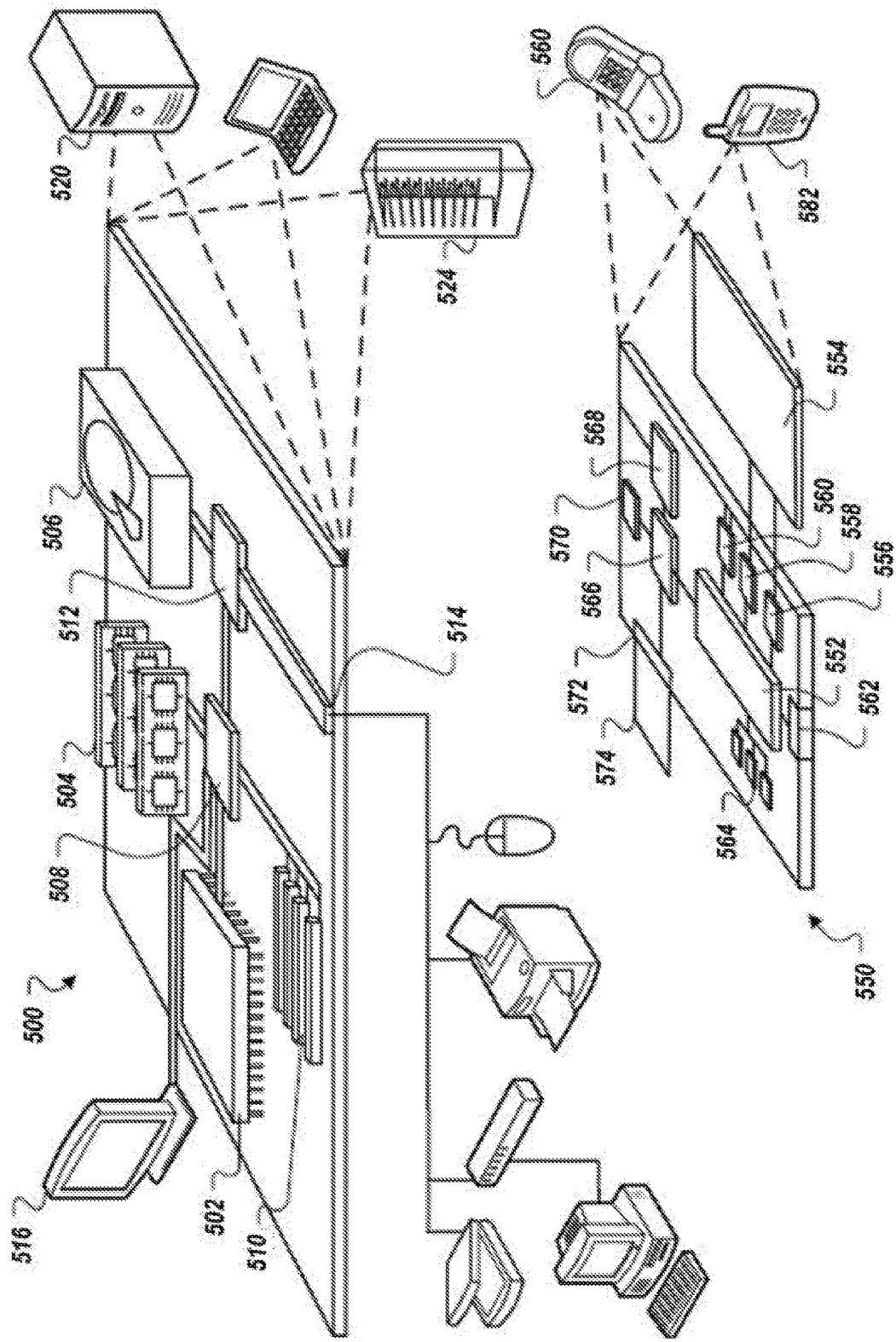
FIG. 5 is a block diagram of an example computing device and an example mobile computing device, for use in illustrative embodiments of the invention.

FIG. 5 shows an example of a computing device 500 and a mobile computing device 550 that can be used in the methods and systems described in this disclosure. The computing device 500 is intended to represent various forms of digital computers, such as laptops, desktops, workstations, personal digital assistants, servers, blade servers, mainframes, and other appropriate computers. The mobile computing device 550 is intended to represent various forms of mobile devices, such as personal digital assistants, cellular telephones, smart-phones, and other similar computing devices. The components shown here, their connections and relationships, and their functions, are meant to be examples only, and are not meant to be limiting.

The computing device 500 includes a processor 502, a memory 504, a storage device 506, a high-speed interface 508 connecting to the memory 504 and multiple high-speed expansion ports 510, and a low-speed interface 512 connecting to a low-speed expansion port 514 and the storage device 506. Each of the processor 502, the memory 504, the storage device 506, the high-speed interface 508, the high-speed expansion ports 510, and the low-speed interface 512, are interconnected using various busses, and may be mounted on a common motherboard or in other manners as appropriate. The processor 502 can process instructions for execution within the computing device 500, including instructions stored in the memory 504 or on the storage device 506 to display graphical information for a GUI on an external input/output device, such as a display 516 coupled to the high-speed interface 508. In other implementations, multiple processors and/or multiple buses may be used, as appropriate, along with multiple memories and types of memory. Also, multiple computing devices may be connected, with each device providing portions of the necessary operations (e.g., as a server bank, a group of blade servers, or a multi-processor system).

The memory 504 stores information within the computing device 500. In some implementations, the memory 504 is a volatile memory unit or units. In some implementations, the memory 504 is a non-volatile memory unit or units. The memory 504 may also be another form of computer-readable medium, such as a magnetic or optical disk.

The storage device 506 is capable of providing mass storage for the computing device 500. In some implementations, the storage device 506 may be or contain a computer-readable medium, such as a floppy disk device, a hard disk device, an optical disk device, or a tape device, a flash memory or other similar solid state memory device, or an array of devices, including devices in a storage area network or other configurations. Instructions can be stored in an information carrier. The instructions, when executed by one or more processing devices (for example, processor 502), perform one or more methods, such as those described above. The instructions can also be stored by one or more storage devices such as computer- or machine-readable mediums (for example, the memory 504, the storage device 506, or memory on the processor 502).

The high-speed interface 508 manages bandwidth-intensive operations for the computing device 500, while the low-speed interface 512 manages lower bandwidth-intensive operations. Such allocation of functions is an example only. In some implementations, the high-speed interface 508 is coupled to the memory 504, the display 516 (e.g., through a graphics processor or accelerator), and to the high-speed expansion ports 510, which may accept various expansion cards (not shown). In the implementation, the low-speed interface 512 is coupled to the storage device 506 and the low-speed expansion port 514. The low-speed expansion port 514, which may include various communication ports (e.g., USB, Bluetooth®, Ethernet, wireless Ethernet) may be coupled to one or more input/output devices, such as a keyboard, a pointing device, a scanner, or a networking device such as a switch or router, e.g., through a network adapter.

The computing device 500 may be implemented in a number of different forms, as shown in the figure. For example, it may be implemented as a standard server 520, or multiple times in a group of such servers. In addition, it may be implemented in a personal computer such as a laptop computer 522. It may also be implemented as part of a rack server system 524. Alternatively, components from the computing device 500 may be combined with other components in a mobile device (not shown), such as a mobile computing device 550. Each of such devices may contain one or more of the computing device 500 and the mobile computing device 550, and an entire system may be made up of multiple computing devices communicating with each other.

The mobile computing device 550 includes a processor 552, a memory 564, an input/output device such as a display 554, a communication interface 566, and a transceiver 568, among other components. The mobile computing device 550 may also be provided with a storage device, such as a micro-drive or other device, to provide additional storage. Each of the processor 552, the memory 564, the display 554, the communication interface 566, and the transceiver 568, are interconnected using various buses, and several of the components may be mounted on a common motherboard or in other manners as appropriate.

The processor 552 can execute instructions within the mobile computing device 550, including instructions stored in the memory 564. The processor 552 may be implemented as a chipset of chips that include separate and multiple analog and digital processors. The processor 552 may provide, for example, for coordination of the other components of the mobile computing device 550, such as control of user interfaces, applications run by the mobile computing device 550, and wireless communication by the mobile computing device 550.

The processor 552 may communicate with a user through a control interface 558 and a display interface 556 coupled to the display 554. The display 554 may be, for example, a TFT (Thin-Film-Transistor Liquid Crystal Display) display or an OLED (Organic Light Emitting Diode) display, or other appropriate display technology. The display interface 556 may comprise appropriate circuitry for driving the display 554 to present graphical and other information to a user. The control interface 558 may receive commands from a user and convert them for submission to the processor 552. In addition, an external interface 562 may provide communication with the processor 552, so as to enable near area communication of the mobile computing device 550 with other devices. The external interface 562 may provide, for example, for wired communication in some implementations, or for wireless communication in other implementations, and multiple interfaces may also be used.

The memory 564 stores information within the mobile computing device 550. The memory 564 can be implemented as one or more of a computer-readable medium or media, a volatile memory unit or units, or a non-volatile memory unit or units. An expansion memory 574 may also be provided and connected to the mobile computing device 550 through an expansion interface 572, which may include, for example, a SIMM (Single In Line Memory Module) card interface. The expansion memory 574 may provide extra storage space for the mobile computing device 550, or may also store applications or other information for the mobile computing device 550. Specifically, the expansion memory 574 may include instructions to carry out or supplement the processes described above, and may include secure information also. Thus, for example, the expansion memory 574 may be provided as a security module for the mobile computing device 550, and may be programmed with instructions that permit secure use of the mobile computing device 550. In addition, secure applications may be provided via the SIMM cards, along with additional information, such as placing identifying information on the SIMM card in a non-hackable manner.

The memory may include, for example, flash memory and/or NVRAM memory (non-volatile random access memory), as discussed below. In some implementations, instructions are stored in an information carrier and, when executed by one or more processing devices (for example, processor 552), perform one or more methods, such as those described above. The instructions can also be stored by one or more storage devices, such as one or more computer- or machine-readable mediums (for example, the memory 564, the expansion memory 574, or memory on the processor 552). In some implementations, the instructions can be received in a propagated signal, for example, over the transceiver 568 or the external interface 562.

The mobile computing device 550 may communicate wirelessly through the communication interface 566, which may include digital signal processing circuitry where necessary. The communication interface 566 may provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), among others. Such communication may occur, for example, through the transceiver 568 using a radio-frequency. In addition, short-range communication may occur, such as using a Bluetooth®, Wi-Fi™, or other such transceiver (not shown). In addition, a GPS (Global Positioning System) receiver module 570 may provide additional navigation- and location-related wireless data to the mobile computing device 550, which may be used as appropriate by applications running on the mobile computing device 550.

The mobile computing device 550 may also communicate audibly using an audio codec 560, which may receive spoken information from a user and convert it to usable digital information. The audio codec 560 may likewise generate audible sound for a user, such as through a speaker, e.g., in a handset of the mobile computing device 550. Such sound may include sound from voice telephone calls, may include recorded sound (e.g., voice messages, music files, etc.) and may also include sound generated by applications operating on the mobile computing device 550.

The mobile computing device 550 may be implemented in a number of different forms, as shown in the figure. For example, it may be implemented as a cellular telephone 580. It may also be implemented as part of a smart-phone 582, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

Constructive Example

Figure 7:
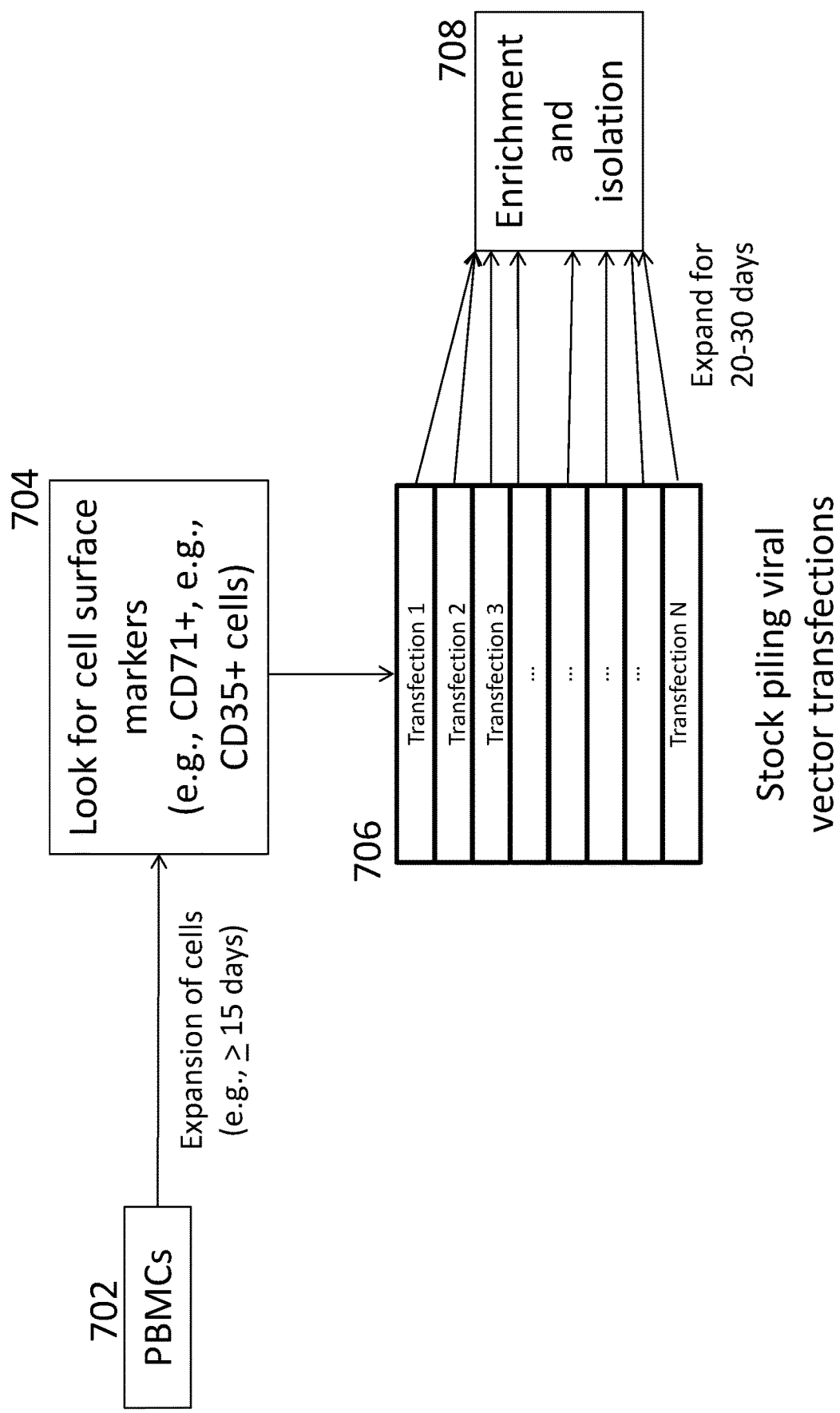
FIG. 7 shows an exemplary "stock piling" schematic of combinatorial and multiplexed viral transductions in peripheral mononuclear blood cells (PBMCs) simultaneously, according to an illustrative embodiment of the invention.

The present constructive example illustrates a system and method for combinational and multiplexed viral transduction (e.g., stock piling) that significantly decreases time and cost of analyzing effects of delivered genes to cells (e.g., peripheral blood mononuclear cells (PBMCs)) (see FIG. 7).

Figure 8:
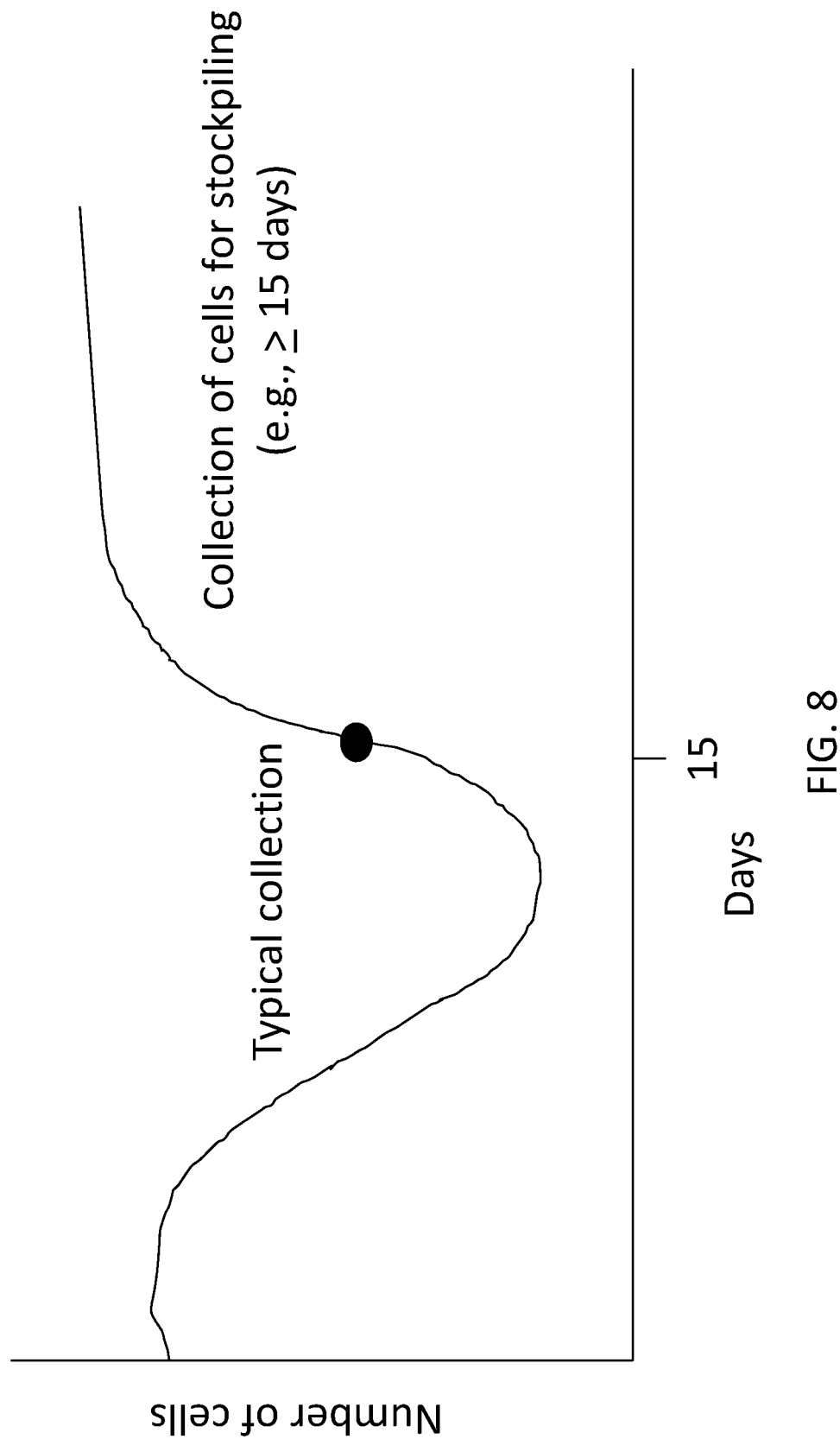
FIG. 8 shows a schematic that depicts a growth curve of cells, according to an illustrative embodiment of the invention. The present disclosure describes that collection of expanded cells occurs at greater than 15 days (e.g., greater than 30 days, e.g., greater than 60 days, e.g., greater than 90 days) for stockpiling transfection of a plurality of vectors, according to an illustrative embodiment of the present invention.
Figure 9:
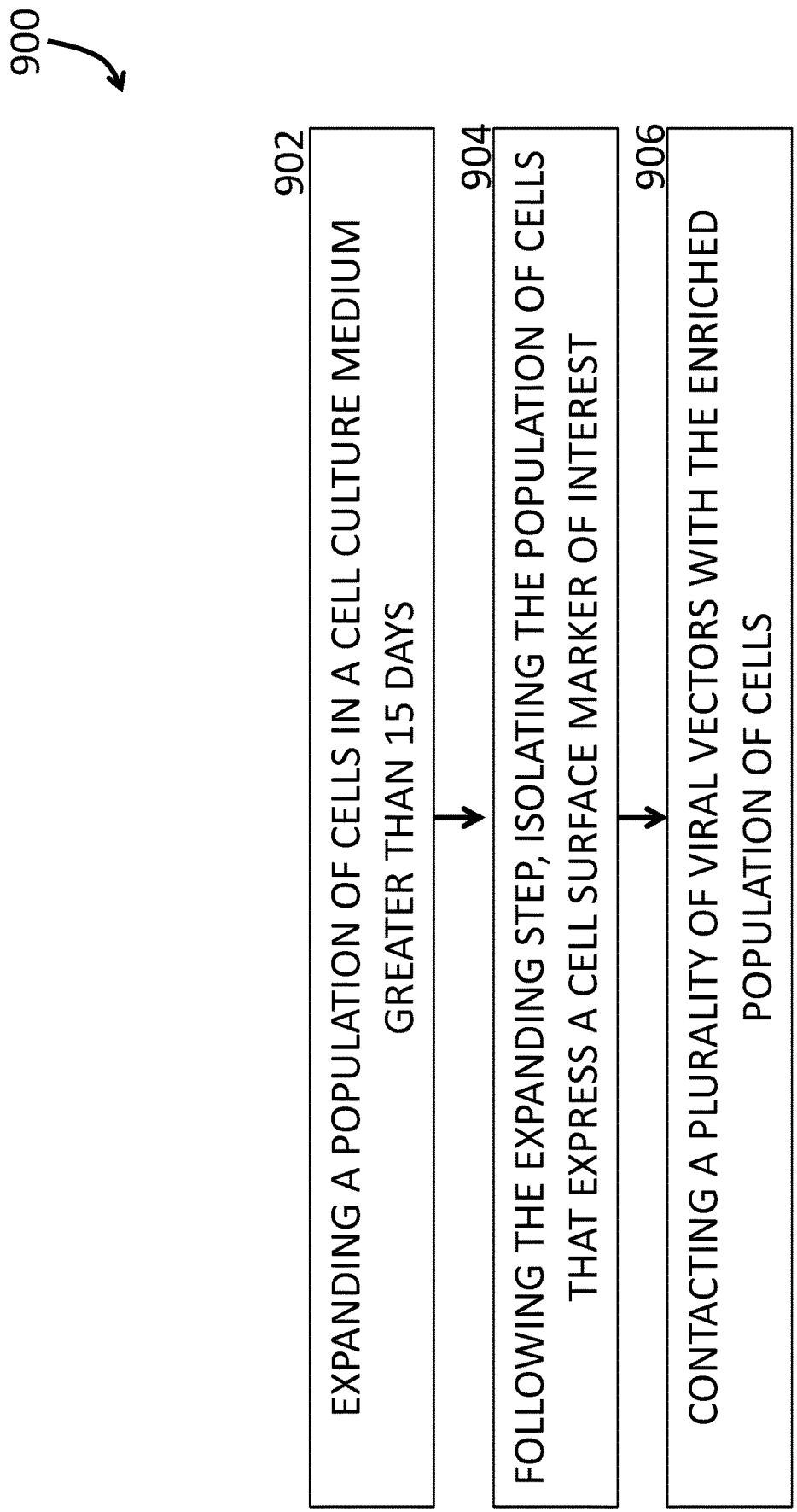
FIG. 9 shows a method of stockpiling a plurality of viral vector transfections across the population of cells, according to an illustrative embodiment of the invention.

Transduction of PBMCs 702 with a viral vector typically occurs at 15 days after expansion of the cells (see FIG. 8). While the number of cells after 15 days is sufficient for transduction using one type of viral vector, the number of cells required for high-throughput and combinatorial viral vector transfection is much greater. Accordingly, according to the present disclosure, PBMCs can be expanded for a time that is greater than 15 days (e.g., at least 30 days, e.g., at least 45 days, e.g., at least 60 days, e.g., at least 90 days) prior to transducing the cells with a plurality of viral vectors. Expansion beyond 15 days provides a number of cells required for stock piling and high-throughput testing, for example, in a 384 well plate.

After initial expansion of PBMCs (e.g., greater than 15 days), surface proteins positive for CD71 or CD36, for example, are used to enrich cells to be transduced with a plurality of viral vectors comprising a plurality of genes of interest (e.g., genes related to cell cycle) (in a setup referred to as "stock piling") (704 and 706 collectively). After about 20 to about 30 days (for example), PBMCs are isolated and tested 708 for effects of combinatorial and multiplexed transduction of viral vectors (e.g., using a multi-well plate with a higher number of wells, e.g., 96-well plate or 384-well plate). This high-throughput and stockpiling approach provides the ability to screen various genes (e.g., related to cell cycle) in the time it typically takes to transduce a population of cells with one type of viral vector.

Equivalents

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for isolating and producing induced pluripotent stem cells (iPSCs), the method comprising:
   providing a colony of cells having been contacted with one or more vectors;
   detecting a plurality of cell surface markers expressed on the surface of the iPSCs, wherein each of the plurality of cell surface markers is indicative of the one or more vector contacted with the colony of cells;
   mapping, by a processor of a computer device based on binding specificity, a plurality of candidate binding agents to the plurality of cell surface markers;
   selecting at least one of the mapped plurality of candidate binding agents for specific binding to at least one of the plurality of cell surface markers expressed on the surface of the iPSCs;
   contacting the colony of cells with the at least one of the selected binding agents; and
   separating the iPSCs bound to the selected binding agents from the colony of cells.

2. The method of claim 1, wherein the colony of cells comprises somatic cells.

3. The method of claim 1, wherein each vector of the one or more vectors comprises multiple vector families.

4. The method of claim 1, wherein the plurality of candidate binding agents comprise one or more members selected from the group consisting of an antibody, a biotinylated bead, a hydrophobic bead, and a magnetic nanoparticle.

5. The method of claim 1, wherein separating the iPSCs bound to the selected binding agents from the colony of cells comprises:
separating the iPSCs into vector-based lineages using one or more members selected from the group consisting of single bead separation, column chromatography, serial separation, microfluidic channel separation, magnetic bead binding, fluorescence activated cell (FACS) sorting, and antibody binding.

6. The method of claim 1, further comprising:
determining, by the processor, a prescribed order in which the selected binding agents are to be contacted with the colony of cells for desired specific binding.

7. The method of claim 1, further comprising:
generating one or more isolated homogeneous colonies of iPSCs from a single vector lineage.

8. The method of claim 7, wherein the one or more isolated homogeneous colonies of iPSCs comprise a genetic variant of the colony of cells.

9. The method of claim 7, wherein the one or more isolated homogeneous colonies of iPSCs are vector-free.

10. The method of claim 1, wherein the plurality of cell surface markers is produced by one or more members selected from the group consisting of Paramyxoviridae virus vector family, Retroviridae virus vector family, Parvoviridae virus vector family, and a non-natural engineering vector.

11. The method of claim 10, wherein the plurality of cell surface markers is produced by Paramyxoviridae virus vector family and wherein the Paramyxoviridae virus vector family comprises one or more members selected from the group consisting of Atlantic salmon paramyxovirus, Newcastle disease virus, Mumps virus, Ferlavirus, Hendravirus, Nipahvirus, Measels, Sendai, Avian pneumovirus, Tioman virus, and TPMV-like virus.

12. The method of claim 11, wherein the plurality of cell surface markers comprise one or more members selected from the group consisting of Nucleocapsid protein (NP), Phosphoprotein (P), Matrix protein (M), Fusion protein (F), and Hemagglutinin-Neuraminidase (HN), Large protein (L).

* * * * *